United States Patent
Dell

(10) Patent No.: US 10,391,045 B2
(45) Date of Patent: Aug. 27, 2019

(54) COMPOSITION CONTAINING P-MENTHANE-3, 8-DIOL AND ITS USE AS INSECT REPELLANT

(76) Inventor: Ian Thomas Dell, Darlington (GB)

(*) Notice: Subject to any disclaimer, the term of this patent is extended or adjusted under 35 U.S.C. 154(b) by 1148 days.

(21) Appl. No.: 12/677,714

(22) PCT Filed: Sep. 12, 2008

(86) PCT No.: PCT/GB2008/003113
§ 371 (c)(1),
(2), (4) Date: Jun. 29, 2010

(87) PCT Pub. No.: WO2009/034352
PCT Pub. Date: Mar. 19, 2009

(65) Prior Publication Data
US 2010/0278755 A1    Nov. 4, 2010

(30) Foreign Application Priority Data

Sep. 13, 2007 (GB) .................................. 0717782.7
Mar. 27, 2008 (GB) .................................. 0805561.8

(51) Int. Cl.
| | | |
|---|---|---|
| *A01N 43/16* | (2006.01) | |
| *A61K 8/34* | (2006.01) | |
| *A01N 31/06* | (2006.01) | |
| *A61K 8/49* | (2006.01) | |
| *A61Q 17/02* | (2006.01) | |

(52) U.S. Cl.
CPC .............. *A61K 8/347* (2013.01); *A01N 31/06* (2013.01); *A61K 8/498* (2013.01); *A61Q 17/02* (2013.01)

(58) Field of Classification Search
CPC .................................................. A61Q 17/02
See application file for complete search history.

(56) References Cited

U.S. PATENT DOCUMENTS

| 5,298,250 A | * | 3/1994 | Lett et al. ................... 424/405 |
| 5,959,161 A | | 9/1999 | Kenmochi et al. |
| 6,337,071 B1 | * | 1/2002 | Molyneux ................... 424/745 |

FOREIGN PATENT DOCUMENTS

| EP | 1567013 B1 | 4/2007 |
| EP | 1412314 B1 | 11/2009 |
| GB | 2282534 A | 4/1995 |
| HU | 0203986 A2 | 5/2005 |
| WO | WO 03/011805 A1 | 4/2004 |
| WO | WO 2004/039158 A1 | 8/2005 |

OTHER PUBLICATIONS

International Search Report dated Jan. 29, 2009, for PCT Application No. PCT/GB2008/003113, 3 pages.
Written Opinion dated Jan. 29, 2009, for PCT Application No. PCT/GB2008/003113, 6 pages.
P. Barbier and G. Leser, Compt. Rend, 1896, vol. 124, p. 1308.
Govere et al., "Efficacy of three insect repellents against the malaria vector *Anopheles arabiensis*," Medical and Veterinary Entomology (2000); 14: 441-444.
Moore et al., "Field Evaluation of Three Plant-Based Insect Repellents Against Malaria Vectors in Vaca Diez Province, the Bolivian Amazon," Journal of the American Mosquito Control Association, 18(2): 107-110, 2002.
Trigg et al., "Laboratory Evaluation of a Eucalpytus-based Repellent against Four Biting Arthropods," Phytotherapy Research, 10: 313-316, 1996.
Trigg, "Evaluation of a Eucalyptus-Based Repellent Against *Anopheles* Spp. in Tanzania," Journal of the American Mosquito Control Association, 12(2): 243-246, 1996.
O. Wallach, Ann., 1908, vol. 360, p. 102.
Zimmerman et al., "Stereoismerism of Isopulegol Hydrates and Some Analogous 1,3-Diols," Journal of the American Chemical Society, May 20, 1953, 75; 2367-2370.

* cited by examiner

*Primary Examiner* — Kyle A Purdy
(74) *Attorney, Agent, or Firm* — Goodwin Procter LLP

(57) ABSTRACT

An economical and simple method of producing para-menthane-3,8-diol in relatively high yield is disclosed. The product is useful as a repellent against noxious insects and other arthropods.

9 Claims, No Drawings

COMPOSITION CONTAINING P-MENTHANE-3, 8-DIOL AND ITS USE AS INSECT REPELLANT

REFERENCE TO RELATED APPLICATIONS

This application is the U.S. national stage of international patent application PCT/GB2008/003113, filed Sep. 12, 2008, which claims the benefit of and priority to GB Patent Application No. 0717782.7, filed on Sep. 13, 2007, and GB Patent Application No. 0805561.8, filed on Mar. 27, 2008.

FIELD OF INVENTION

This invention relates to improvements in p-menthane-3,8-diol compositions, to a novel method for effectively and economically producing p-menthane-3,8-diol and more particularly to a method of controlling the formation of unwanted by-products. The process uses citronellal or citronella bearing essential oils as raw material.

BACKGROUND TO THE INVENTION

Extracts of the lemon eucalyptus plant *Corymbia citriodora* (*Eucalyptus citriodora, Eucalyptus maculate* var. *citriodora*) have been used in China under the name Quwenling for the purposes of repelling mosquitoes (Li et al, 1974 Studies on the Repellent Quwenling, Malaria Res., p. 6). The major active repellent ingredient of these extracts has been demonstrated to be p-menthane-3,8-diol (Trigg and Hill, (1996) *J Am. Mosq. Control Assoc.,* 12, 243-246; Trigg and Hill (1996) *Phytother., Res.,* 10, 313-316; Govere et al, (2000), *Med., Vet., Entomol.,* 14, 441-444: Moore et al, (2002 *J. Am. Mosq. Control Assoc.,* 18, 107-110).

Although p-menthane-3,8-diol may be obtained by extraction from the leaves of *Corymbia* spp., this is economically restricted to the places the plants are growing in sufficient quantity to be commercially viable. As a result, methods of producing p-methane-3,8-diol by chemical synthesis have been proposed.

An early monograph on the synthesis of p-menthane-3,8-diol is given by P. Barbier and G. Leser (1896) (*Compt. Rend* 124, 1308) who obtain p-menthane-3,8-diol together with isopulegole on the cyclisation of citronellal in dilute sulphuric acid. The reaction probably follows two stages: first the cyclisation of citronellal to isopulegole followed by hydration of the latter material top-menthane-3,8-diol (O. Wallach, *Ann.,* 1908, 360, 102). No mention is made in these early reports of any potential use for the resultant diol.

An essentially similar cyclisation/hydration procedure is described by Zimmerman and English in *J. Am. Chem. Soc.,* 75, 2367 (1953) and this process is followed in U.S. Pat. No. 5,298,250 (R&C Products PTY Ltd) which claims an insect repellent comprising p-menthane-3,8-diol with "synergist acetals", these acetals are the condensation products of the citronellal starting material and the p-menthane-3,8-diol resulting from the reaction. Although not exhibiting any insect repellent activities per se, U.S. Pat. No. 5,298,250 states that there is a synergism in the insect repellent activity when these acetal compounds are in combination with p-menthane-3,8-diol. The present inventors have been unable to demonstrate such an effect.

U.S. Pat. No. 5,959,161 (Takasago International Corporation) claims a method of producing p-menthane-3,8-diol by treating citronellal with very dilute sulphuric acid but, in other respects, it is essentially the same as the Barbier and Leser method. The claimed high purity of the final p-menthane-3,8-diol is a result of a solvent extraction and recrystallisation procedure.

Thus, compositions comprising p-menthane-3,8-diol are well known. However, physico chemical limitations exist as to the concentration of p-menthane-3,8-diol that may be used in a composition and therefore the efficacy of commercially available products. One major disadvantage of known p-menthane-3,8-diol compositions is that at a concentration of 60% w/w, the p-menthane-3,8-diol becomes supersaturated and therefore crystals will begin to form. Conventionally known products usually avoid this problem by use of a solvent, such as dipropylene glycol and/or by the use of lower concentrations, in the region of 45 to 50%.

We have now surprisingly found a novel composition and a novel process of preparation of p-menthane-3,8-diol which overcomes or mitigates the disadvantages of prior art compositions and process.

SUMMARY OF INVENTION

Therefore, one object of the present invention is to produce a liquid grade of p-menthane-3,8-diol suitable for use as an insect repellent by a simple low cost method and/or to provide a high concentration composition that will have improved efficacy when compared to conventionally know p-menthane-3,8-diol compositions. The end product contains controlled amounts of inactive by-products and is suitable for use as basis for an insect repellent. The method of this invention is the cyclisation and hydration of citronellal with acid containing a phase transfer catalyst. By controlling the reaction conditions it is possible to control the formation of inactive by-products. Surprisingly, by suitable reaction control the end product remains in liquid form. The end product comprises mainly para-menthane-3,8-diol, the acetal formed by the reaction of para-menthane-3,8-diol with citronellal (hereinafter referred to as PMD-citronellal acetal), isopulegol and small amounts of citronellal.

Generally, p-menthane-3,8-diol (I) is formed by the reaction of citronellal (II) with dilute sulphuric acid:

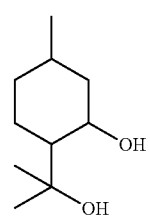

I

The usually undesirable PMD-citronellal acetal (III) is formed by the reaction of the product p-menthane-3,8-diol (I) with citronellal (II):

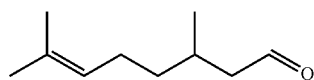

II

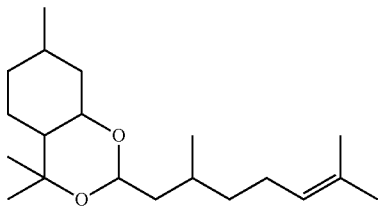

III

Using conventional methods, the amount of PMD-citronellal acetal (III) produced is usually in the region of from 5% to 8% w/w.

We have found that by incorporating larger amounts of PMD-citronellal acetal in the composition, the solubilisation of the p-menthane-3,8-diol is increased.

Thus, according to a first aspect of the invention we provide a composition comprising from 70 to 85% w/w of p-menthane-3,8-diol and from 7 to 15% w/w of PMD-citronellal acetal (III).

The more efficacious compositions are preferred and therefore, preferably the amount of p-menthane-3,8-diol is from 75 to 85% w/w.

The amount of PMD-citronellal acetal (III) may preferably be from 10 to 15% w/w, more preferably 12 to 15% w/w and especially 14 to 15% w/w.

It is apparent in the composition of the invention that the PMD-citronellal acetal (III) essentially acts as a solvent towards of p-menthane-3,8-diol. Thus, according to a yet further aspect of the invention we provide the use of PMD-citronellal acetal (III) as a solvent. We especially provide the use of PMD-citronellal acetal (III) as a solvent to p-menthane-3,8-diol.

Thus, it will be understood by the person skilled in the art that PMD-citronellal acetal (III) could be separately added to the composition of the invention. However, it is a further novel aspect of the present invention to provide a method of preparation of p-menthane-3,8-diol in which the amount of PMD-citronellal acetal (III) in the end product may be controlled. Thus, according to a further aspect of the invention we provide a method for producing para-menthane-3,8-diol comprising the step of treating citronellal with an acid in the presence of a phase transfer catalyst to produce p-menthane-3,8-diol.

Acetal by-products are common in reactions of alcohols with aldehydes and are difficult to avoid. The inclusion of a phase transfer catalyst, together with control of reaction conditions, can limit acetal formation. Moreover, it is possible to control the reaction to form an end product which remains liquid under ambient conditions. This can be advantageous during subsequent utilisation of the reaction mixture in the preparation of insect repellent products.

Preferably, the method of the invention comprises conducting the reaction in an aqueous or substantially aqueous reaction mixture. The source of citronellal may be, for example, citronellal bearing essential oils.

The method of the invention is further advantageous in that it enables the control of levels of other impurities in the product. In particular the level of citronellol may be controlled and may therefore be less than 1% w/w, preferably less than 0.75% w/w, more preferably less than 0.5% w/w and most preferably citronellol is absent or at least undetectable using conventional methods known per se, for example, gas-liquid chromatography.

Therefore, according to a further aspect of the invention we provide a composition as hereinbefore described in which the level of citronellol is less than 1% w/w, preferably less than 0.75% w/w, more preferably less than 0.5% w/w and most preferably citronellol is absent or at least undetectable using conventional methods known per se, for example, gas-liquid chromatography.

According to a further aspect of the invention we provide an insect repellent formulation which comprises a p-menthane-3,8-diol composition as hereinbefore described, in combination with a suitable adjuvant, diluent or carrier.

A further disadvantage with known compositions comprising, for example, p-menthane-3,8-diol, is that such compositions have a strong odour, e.g. a lemony odour. Therefore, known compositions are unsuitable for including any additional scent or aromatic oil as the odour would be masked by the lemony odour of the active ingredient. Thus, the method of the present invention is especially advantageous in that, inter alia, volatile odiferous impurities may be avoided or removed from the end-product. Particular volatile odiferous impurities which may be mentioned include, for example, citronellol (3,7-dimethyl-oct-6-en-1-ol); 1,8-cineol (1,3,3-trimethyl-2-oxabicyclo[2.2.2]octane); citronellyl acetate (acetic acid 3,7-dimethyl-oct-6-enyl ester); linalol (3,7-dimethyl-octa-1,6-dien-3-ol); β-pinene (6,6-dimethyl-2-methylene-bicyclo[3.1.1]heptane); α-terpinol (2-(4-methyl-cyclohex-3-enyl)-propan-2-ol); d-limonene (4-isopropenyl-1-methyl-cyclohexene); citronellal (3,7-dimethyloct-6-en-1-al); geranial (3,7-dimethyl-2,6-octadienal) and geraniol (3,7-dimethyl-2,6-octadien-1-ol).

Thus, the composition of the invention is advantageous in that the levels of the odiferous impurities may be minimised. Therefore, according to a further aspect of the invention we provide a composition as hereinbefore described wherein the amount of citronellol is less than 5% w/w.

Alternatively, we provide a composition as hereinbefore described wherein the amount of 1,8-cineol is less than 0.1% w/w.

Alternatively, we provide a composition as hereinbefore described wherein the amount of citronellyl acetate is less than 0.1% w/w.

Alternatively, we provide a composition as hereinbefore described wherein the amount of linalol is less than 0.1% w/w.

Alternatively, we provide a composition as hereinbefore described wherein the amount of β-pinene is less than 0.1% w/w.

Alternatively, we provide a composition as hereinbefore described wherein the amount of α-terpinol is less than 0.1% w/w.

Alternatively, we provide a composition as hereinbefore described wherein the amount of d-limonene is less than 0.05% w/w.

Alternatively, we provide a composition as hereinbefore described wherein the amount of geranial is less than 0.1% w/w.

Alternatively, we provide a composition as hereinbefore described wherein the amount of geraniol is less than 0.1% w/w.

In an especially preferred aspect of the invention we provide a composition as hereinbefore described wherein the amount of amounts of citronellol is less than 5% w/w, 1,8-cineol is less than 0.1% w/w, citronellyl acetate is less than 0.1% w/w, linalol is less than 0.1% w/w, β-pinene is less than 0.1% w/w, α-terpinol is less than 0.1% w/w, d-limonene is less than 0.05% w/w, geranial is less than 0.1% w/w and geraniol is less than 0.1% w/w.

Thus, the formulation of the invention may include, for example, a fragrance compound or a perfume composition. The fragrance compound or perfume composition may comprise one or more essential oils and/or active ingredients of essential oils. An essential oil includes any type of volatile oil that is obtained from a plant and possesses the odour and other characteristic properties of the plant. Examples of useful essential oils include: almond bitter oil, anise oil, basil oil, bay oil, caraway oil, cardamom oil, cedar oil, celery, oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronellal, methyl salicylate, ethyl salicylate, propyl salicylate, citronellol, safrole, and limonene.

It will be understood by the person skilled in the art that the repellent composition or formulation of the invention may be used as a repellent against a variety of blood-feeding insects and arthropods such as biting flies, mite, midges, fleas, mosquitoes, ticks and lice and the reference to "insect repellent" should be construed accordingly.

The composition or formulation of the invention may be applied topically to the skin, hide, hair, fur, feathers or other surface of a mammal, such as a human or domesticated animal, that serves as a host for an insect as hereinbefore defined. Thus, the formulation of the invention will preferably include a dermatologically acceptable adjuvant, diluent or carrier. Such a carrier may, for example, be selected form the group consisting of water, alcohol, silicone, petrolatum, lanolin; or an organic liquid carrier, such as a liquid aliphatic hydrocarbon (e.g. pentane, hexane, heptane, nonane, decane, etc) or a liquid aromatic hydrocarbon.

Other suitable carriers include silicone, petrolatum, lanolin, liquid hydrocarbons, agricultural spray oils, paraffin oil, tall oils, liquid terpene hydrocarbons and terpene alcohols, aliphatic and aromatic alcohols, esters, aldehydes, ketones, mineral oil, higher alcohols, finely divided organic and inorganic solid materials. In addition to the above-mentioned liquid hydrocarbons, the carrier can contain conventional emulsifying agents which can be used for causing the active ingredient to be dispersed in, and diluted with, water for end-use application. Still other liquid carriers can include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Conventional aromatic and aliphatic esters, aldehydes and ketones can be used as carriers, and occasionally are used in combination with the above-mentioned alcohols. Still other liquid carriers include relatively high-boiling petroleum products such as mineral oil and higher alcohols (such as cetyl alcohol). Additionally, conventional or so-called "stabilizers" (e.g. tert-butyl sulfinyl dimethyl dithiocarbonate) can be used in conjunction with, or as a component of, the carrier or carriers used in a composition as made according to this invention.

The topically administered formulation of the invention may be formulated as one or more of a body wash, rinse, lotion, splash, tonic or toner, bath and shower gels, foam products (e.g. shaving foams), makeup, deodorants, shampoo, hair lacquers/hair rinses, personal soap compositions (e.g. hand soaps and bath/shower soaps) or other personal care treatments or palliatives, and cleaning agents such as detergents and solvents, and air fresheners and odour removers. Such products may be fabricated, for example, in the form of a sprayable liquid, an aerosol, a foam, a cream, an ointment, a gel, a paste, a powder or a friable solid.

The formulation of the invention may also contain other therapeutically or cosmetically active adjuvants or supplemental ingredients as are typical in the personal care industry. Examples of these include, but shall not be limited to fungicides, sun screening agents, sun blocking agents, vitamins, tanning agents, plant extracts, anti-inflammatory agents, anti-oxidants, radical scavenging agents, retinoids, alpha-hydroxy acids, antiseptics, antibiotics, antibacterial agents, antihistamines; adjuvants such as thickeners, buffering agents, chelating agents, preservatives, gelling agents, stabilizers, surfactants, emolients, colouring agents, aloe vera, waxes, and penetration enhancers; and mixtures thereof.

DETAILED DESCRIPTION OF THE INVENTION

The citronellal used as a raw material in this invention may be obtained by purifying essential oils which contain citronellal such as citronella oil (from *Cymbopogon nardus, Cymbopogon winternianus*), *Corymbia citriodora* (*Eucalyptus citriodora, Eucalyptus maculate* var. *citriodora*), from lemon balm oil (*Melissa officinalis*) or by any other means.

It is convenient for the method of this invention to utilise lemon eucalyptus oil which is stripped of lower boiling components including limonene (dipentene), 1,8-cineole and citronellol by distillation. The resultant refined oil contains typically 85-90 percent citronellal with the remainder being almost entirely isopulegole (7.2-14.4 percent).

In order to obtain an end product with a high amount of para-menthane-3,8-diol and a low amount of acetal by-products it is advantageous to avoid contact of the para-menthane-3,8-diol and un-reacted citronellal in the reaction mix. This is achieved in the method of this invention by controlling the addition of citronellal containing oil to the acid, combined with efficient stirring to finely disperse the oil and maintaining the fine dispersion by means of a surface active phase transfer catalyst.

A method for carrying out this invention is as indicated below. The actual detail of the processing will be known to those skilled in the art:

1. A solution of hexadecyltrimethylammonium bromide (0.05%) in 5% sulphuric was charged into a reactor and vigorously stirred. Citronellal in an amount equivalent to 33.32. % of the total charge was fed into the reactor over a five hour period with the temperature being maintained at or below 35° C. Stirring was continued for a further three hours.
2. The stirring was stopped and the two phases were allowed to separate. The lower aqueous acid solution was run off to be used in further batches. The temperature should be maintained above 30° C. for ease of separation.
3. The organic layer was washed with a solution of mild alkali such as sodium carbonate or sodium bicarbonate to remove residual acid until an aliquot shaken with water showed a pH of 5.0-8.0. The product was filtered through a 100 μM filter to remove residual water and any suspended solids.

4. The resultant product is a clear or slightly opaque almost colourless, moderately viscous liquid with a slight pleasant floral odour quite unlike that of the starting material.

Analysis of the product of the above process shows a typical composition:

| | |
|---|---|
| PMD-citronellal acetal | 5-12% |
| Isopulegole | 7-14% |
| para-menthane-3,8-diol | remainder |

Surprisingly, although para-menthane-3,8-diol is a crystalline material at room temperature which separates as long needle crystals in other methods of synthesis, the method of this invention results in a product which is a viscous liquid. It is believed that the presence of isopulegole and the acetal condensate of citronellal with para-menthane-3,8-diol approximates to a ternary eutectic.

In the method described it will be appreciated that the other strong acids may be utilised for the hydration/cyclisation reactions and that other surface active materials may act as phase transfer catalysts. Examples of other suitable strong acids include hydrochloric acid, phosphoric acid. Alternative phase transfer catalysts include anionic, non-ionic and zwitterionic surface active agents.

As to the ratio of aqueous sulphuric acid to citronellal, it is preferable to use 1 to 10 parts by weight of aqueous sulphuric acid containing the phase transfer catalyst to one part by weight citronellal to obtain para-menthane-3,8-diol in the most suitable ratio together with isopulegole and the acetal and more preferable to use three parts of aqueous sulphuric acid containing the phase transfer catalyst to one part by weight of citronellal or citronellal containing essential oil.

The reaction time is not restricted and it has been found that an addition of the citronellal to the acid/catalyst mixture over a period of three to twelve hours and a further reaction time of one to ten hours, more preferably an addition time of five hours and a further reaction time of three hours gives a product of a suitable composition.

The reaction temperature is preferably between 20° C. and 50° C., more preferable in the range 25° C. to 35° C. Higher temperatures tend increase the condensation of the para-menthane-3,8-diol with citronellal to form the acetal and lower temperatures prolong the reaction time.

Following the washing with alkali solution and removal of any residual aqueous phase, the mixture is of suitable quality for use as an insect repellent without any further purification.

The method of this invention results in a composition containing seventy five percent para-menthane-3,8-diol having excellent repellent action particularly against noxious insects. The method is simple and the para-menthane-3,8-diol is produced in high yield, smoothly and economically without the use of complicated equipment of purification processes using citronellal or citronellal bearing essential oils as raw materials.

The invention will now be illustrated by way of example only.

Example 1

Full batch Analysis for Citrepel 75

| | Batch Reference | | | |
|---|---|---|---|---|
| Component | 14384 | 14490 | 16427 | 17067 |
| beta-pinene | nd | 0.24% | Nd | Nd |
| d-limonene | 0.09% | 0.27% | 0.72% | Nd |
| citronellal | 0.16% | 0.20% | 0.19% | 0.09% |
| 1,8-cineol | nd | nd | Nd | Nd |
| geranial | nd | nd | Nd | 0.12% |
| citronellol | 0.53% | nd | 0.09% | 0.43% |
| geraniol | 0.34% | 0.14% | 0.18% | 0.09% |
| linalol | nd | nd | 1.90% | 0.90% |
| isopulegol | 10.90% | 14.50% | 12.2% | 7.1% |
| p-menthane 3,8-diol comments | | | | fine crystals |
| odour | very low | v slight | Slight | very low |
| colour | | | | |

Whilst the method of this invention has been described with reference to certain embodiments, it will be evident to those skilled in the art that numerous modifications and variations are possible without departing from the spirit or scope of the invention as described.

The invention claimed is:

1. A moderately viscous liquid suitable for being used as an insect repellent, said liquid comprising from 5 to 12% w/w of PMD-citronellal acetal, from 7 to 14% w/w isopulegol and the remainder being p-menthane-3,8-diol, which approximates to a ternary eutectic and is liquid at ambient temperatures.

2. A moderately viscous liquid according to claim 1 wherein the amount of p-menthane-3,8-diol is from 75 to 85% w/w.

3. A moderately viscous liquid according to claim 1 wherein the amounts of citronellol is less than 5% w/w, 1,8-cineol is less than 0.1% w/w, citronellyl acetate is less than 0.1% w/w, linalol is less than 0.1% w/w, β-pinene is less than 0.1% w/w, α-terpinol is less than 0.1% w/w, d-limonene is less than 0.05% w/w, geranial is less than 0.1% w/w and geraniol is less than 0.1% w/w.

4. An insect repellent formulation which comprises a moderately viscous liquid comprising p-menthane-3,8-diol according to claim 1, in combination with a suitable adjuvant, diluent or carrier.

5. An insect repellent formulation according to claim 4 which includes an additional scent or aromatic oil.

6. An insect repellent formulation according to claim 4 wherein the formulation is repellent against one or more of biting flies, mite, midges, fleas, mosquitoes, ticks and lice.

7. An insect repellent formulation according to claim 4 wherein the formulation is for application topically to the skin, hide, hair, fur, feathers or other surface of a mammal.

8. An insect repellent formulation according to claim 4 wherein the formulation comprises one or more of a body wash, rinse, lotion, splash, tonic or toner, bath and shower gels, foam products, makeup, deodorants, shampoo, hair lacquers/hair rinses, personal soap compositions or other personal care treatments or palliatives, and cleaning agents, detergents and solvents, and air fresheners and odour removers.

9. An insect repellent formulation according to claim 4 wherein the formulation is in the form of a sprayable liquid, an aerosol, a foam, a cream, an ointment, a gel, a paste, a powder or a friable solid.

* * * * *